United States Patent [19]

Fenner

[11] Patent Number: 5,783,688

[45] Date of Patent: Jul. 21, 1998

[54] PURIFICATION OF 3'-FDDU AND RESULTANT COMPOSITIONS

[75] Inventor: Simon Fenner, Bristol, United Kingdom

[73] Assignee: Rhone-Poulenc Chemicals Limited, Hertfordshire, United Kingdom

[21] Appl. No.: 545,841

[22] PCT Filed: May 12, 1994

[86] PCT No.: PCT/GB94/01025

§ 371 Date: Dec. 12, 1995

§ 102(e) Date: Dec. 12, 1995

[87] PCT Pub. No.: WO94/26763

PCT Pub. Date: Nov. 24, 1994

[30] Foreign Application Priority Data

May 10, 1993 [GB] United Kingdom .................. 9309787

[51] Int. Cl.⁶ .................................................. C07H 19/073
[52] U.S. Cl. ..................... 536/27.12; 536/27.14; 536/28.53
[58] Field of Search .................. 536/27.12, 27.14, 536/28.53

[56] References Cited

U.S. PATENT DOCUMENTS

| | | | |
|---|---|---|---|
| 5,157,114 | 10/1992 | Rahim et al. | 536/28.54 |
| 5,223,263 | 6/1993 | Hostetler et al. | 424/450 |
| 5,376,644 | 12/1994 | Selway et al. | 514/50 |
| 5,449,664 | 9/1995 | Verheyden et al. | 514/45 |

FOREIGN PATENT DOCUMENTS

| | | |
|---|---|---|
| 0356166 | 2/1990 | European Pat. Off. . |
| 0470355 | 2/1992 | European Pat. Off. . |
| 0495225 | 7/1992 | European Pat. Off. . |

OTHER PUBLICATIONS

Hilgetag et al. (ed.), *Preparative Organic Chemistry*, John Wiley & Sons, New York, NY, 1972, Appendix III(b) and (c), only pp. 1114–1120 supplied.

*Primary Examiner*—John Kight
*Assistant Examiner*—L. Eric Crane
*Attorney, Agent, or Firm*—Burns, Doane, Swecker & Mathis, L.L.P.

[57] ABSTRACT

2',3'-Dideoxy-3'-fluorouridine is purified by treating an aqueous or aqueous methanolic solution with charcoal.

16 Claims, No Drawings

PURIFICATION OF 3'-FDDU AND RESULTANT COMPOSITIONS

The present invention relates to the purification of 2',3'-dideoxy-3'-fluorouridine (3'-FDDU) of formula:

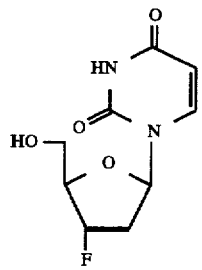

A

2',3'-dideoxy-3'-fluorouridine A is a well known intermediate in the preparation of therapeutically useful ribonucleosides, disclosed in, for example EP-A-305117 and 356166 (Wellcome Foundation).

In order to qualify for use in the pharmaceutical field, it is necessary that the 3'-FDDU meet the required purity specification. Unfortunately however, 3'-FDDU, by whatever method it is produced, often contains impurities which are exceedingly difficult to remove. In addition, coloured impurities are often formed during processing of white, pure 3'-FDDU.

Currently 3'-FDDU is produced by the deprotection of an intermediate of formula:

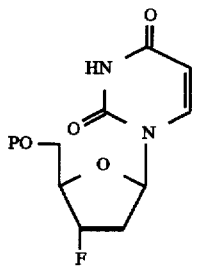

C where P is a protecting group, preferably a 4-methoxybenzoyl radical. 3'-FDDU is recovered by a simple transesterification process using NaOH/MeOH reaction as described in EP-A-0356166.

The aforesaid starting material may be prepared as described in EP-A-0470355, by reaction of a corresponding anhydro-nucleoside with hydrogen fluoride in the presence of an aluminium-containing catalyst.

All known processes for producing 3'-FDDU yield a product containing significant amounts of impurities. The exact nature and identity of the 2 major impurities are known. They are anisic acid of formula:

and a dimer of formula:

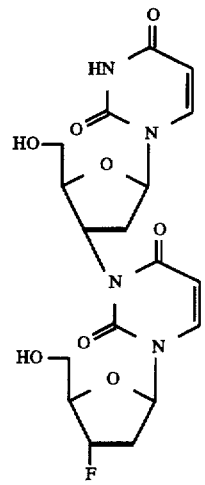

B

In order to meet the high purity standards required for pharmaceutical uses, various methods of purification can be used. These methods, however, often involve extensive and complicated neocrystallizations, solvent extractions, etc., requiring elaborate and costly apparatus and the expenditure of extended periods of time.

The present invention provides a method for the purification of crude 3'-FDDU which is more efficient than those heretofore commonly employed, at a significant saving in time and expense.

The present invention provides a method of purifying crude 3'-FDDU (2'3'-dideoxy-3'-fluorouridine) containing anisic acid and a dimer which comprises contacting an aqueous or aqueous methanolic solution of crude 3'-FDDU with adsorbent carbon. This carbon treatment of crude 3'-FDDU results in a product having a higher degree of purity and whiteness than other, known methods.

Carbon treatment of crude 3'-FDDU solution in accordance with the invention removes a large percentage of the impurities present therein, including the two major impurities: anisic acid and the dimer. The method of the present invention is particularly adapted for the removal of impurities from 3'-FDDU produced by the hydrofluorination, deprotection process starting from 5-O -[4'-methoxybenzoyl]-3'-anhydro-2'-deoxyuridine.

The aforesaid hydrofluorination, deprotection process can be operated to produce directly an aqueous methanolic solution of 3'-FDDU to which the process of the invention can be directly applied. In preferred embodiments of the invention however, the 3'-FDDU is first isolated in crude solid form and this solid is washed with acetone to remove a significant proportion of anisic acid impurity before the 3'-FDDU is dissolved in water or aqueous methanol and contacted with adsorbent carbon. Alternatively, or in addition, the aqueous or aqueous methanolic solution of 3'-FDDU is washed with toluene before it is contacted with the adsorbent carbon: this removes any traces of methyl anisic ester that may be present.

Any substantially pure carbon absorbent material may be employed in the method of the invention. It is a well known type of material and an article of commerce. Such carbon has a large surface area available for the adsorption of impurities. Examples of the carbons which may be utilised are charcoal and bone black. Particularly preferred are the so-called activated carbons (or activated charcoal). Activated carbons are usually produced by heating ordinary carbon to high temperatures, e.g. 80°–900° C., in the presence of steam or carbon dioxide and a hygroscopic substance such as zinc chloride, phosphoric acid or sodium sulfate. Activated carbons are particularly effective for the removal of impurities and colouration from crude 3'-FDDU, as indicated by liquid chromatographic analysis.

Commercially available activated carbons are suitable for use in the invention. Different grades differ somewhat in their effectiveness in removing the impurities and in the extent they reduce the yield of the product by adsorbing 3'-FDDU itself. Suitable industrial activated carbons include Aldrich activated carbon 16,155-1, Sutcliffe and Speakman DCL 226, Norit CA1 and GB1, and Chemviron 114A and PWA. Norit CA1 is currently preferred.

The amount of carbon employed to purify the crude 3'-FDDU is not critical and depends in each application upon the quantity of impurities present therein. Generally, however, an amount of carbon ranging from 0.1% to about 5% by weight based on the amount of solution is sufficient to remove impurities (with a 3'-FDDU concentration between 0.5 to 5% w/w in the solution).

The purification method of the present invention is advantageously carried out by intimately admixing in a suitable container the crude 3'-FDDU aqueous or aqueous-methanolic homogeneous solution and the carbon and slurrying the mixture at room temperature. The pH of the mixture (solution) should preferably be around 2 to 4. The mixture may be heated to a temperature in the range from ambient temperature to 100° C., preferably from about 60° C. to 95° C. to ensure intimate contact between the carbon and the crude 3'-FDDU solution. The contact time may be between 5 min to 120 hours, preferably 1 hour to 4 hours. Subsequently, the carbon is removed from the 3'-FDDU solution-carbon slurry, e.g. by centrifugation or filtration. The purification could also be run in a continuous process using granular carbon in column operation (fixed or moving beds). This offers a more efficient utilisation of the activated carbon and less equipment (no slurry tanks and filter presses).

The 3'-FDDU solution is then cooled, and concentrated under vacuum until the purified 3'-FDDU crystallizes therefrom. The 3'-FDDU crystals may be collected by any convenient method, e.g. filtration, decantation or centrifugation, washed and dried. The 3'-FDDU is thus produced in a highly purified form meeting the pharmaceutical specifications with an expenditure of minimum time and expense.

The invention is illustrated by the following Examples. In the Examples the purity of the various specimens of 3'-FDDU was measured by HPLC on a column of Lichrospher 100 RP 18 (Merck) at room temperature using as mobile phase water/acetonitrile/TFA in the proportions, (As, 95/5/0.1 and (B) 5/95/0.1.

| TIME | % A | % B |
| --- | --- | --- |
| 0 min | 98 | 2 |
| 20 min | 80 | 20 |
| 30 min | 50 | 50 |

Under the conditions used, the retention times were 3'-FDDU, 3 minutes; Anisic acid, 16.6 minutes; Dimer, 9.5 minutes. Detection was by UV absorption at 260 nm.

EXAMPLE 1

Table 1 below summarises the result of heating a crude solution of 3'-FDDU (59.0kg of aqueous methanolic solution containing initially 1.55% w/w 3'-FDDU and 0.024% anisic acid and 0.0235% of dimer B). With 0.5% carbon loading (Aldrich activated carbon, Ref 16,155-1) in 2 hours at room temperature, the anisic acid is totally removed and only ⅔ of the initial dimer quantity remains. With 1% carbon loading in 4 hours, the dimer became only ⅓ of the initial quantity. The final product, recovered after filtration of carbon, concentration under vacuum of the methanolic aqueous solution to crystallize 3'-FDDU, and isolation by filtration of pure 3'-FDDU is a white solid having purity of 98.6% with only 0.4% of dimer and no table anisic acid.

COMPARATIVE EXAMPLE 1

The direct concentration under vacuum of the crude 3'-FDDU methanolic aqueous solution to crystallize 3'-FDDU its isolation of a pale orange 3'-FDDU with a purity (HPLC) of the final product of 95.7% containing 1.6% of dimer B and 1.7% anisic acid. (The manufacturing specification requires less than 1% anisic acid).

TABLE 1

| Sample Number | Carbon loading % (w/w solution) | Elapsed time (hrs) | 3'-FDDU Assay % | Anisic acid (%/FDDU) | Dimer (%/FDDU) |
| --- | --- | --- | --- | --- | --- |
| 1 | 0.0 | 0 | 1.55 | 1.6 | 1.5 |
| 2 | 0.5 | 2.0 | 1.53 | 0.3 | 1.03 |
| 3 | 1.0 | 4.0 | 1.40 | 0.0 | 0.57 |
| 4 | 1.5 | 7.0 | 1.33 | 0.0 | 0.39 |

EXAMPLE 2

With the same carbon treatment (using Aldrich activated carbon, Ref 16,155-1) on another crude 3'-FDDU solution (1.50% 3'-FDDU w/w) containing a high level of Anisic acid and Dimer (see Table 2), a similar result was obtained using 1.5% carbon loading.

TABLE 2

CARBON TREATMENT ON CRUDE 3'-FDDU
(input weight of solution: 56.2 kg)

| Sample Number | Carbon loading % (w/w solution) | Elapsed time (hrs) | 3'-FDDU Assay % | Anisic acid (%/FDDU) | Dimer (%/FDDU) |
| --- | --- | --- | --- | --- | --- |
| 1 | 0 | 0.0 | 1.50 | 1.7 | 1.5 |
| 2 | 0.18 | 1.0 | 1.47 | 1.0 | 1.5 |
| 3 | 1.5 | 4.0 | — | 0.0 | 0.88 |

Table 3 demonstrates, with another crude solution, influence of the time of contact and the reproducibility of the result.

TABLE 3

CARBON TREATMENT ON CRUDE 3'-FDDU
(input weight of solution: 54.5 kg)

| Sample Number | Carbon loading % (w/w solution) | Elapsed time (hrs) | 3'-FDDU Assay % | Anisic acid (%/FDDU) | Dimer (%/FDDU) |
| --- | --- | --- | --- | --- | --- |
| 1 | 0 | 0 | 1.50 | 1.7 | 1.5 |
| 2 | 1.5 | 12.0 | — | <0.1 | 0.7 |

EXAMPLE 3

Carbon adsorption isotherms have been measured for 5 samples obtained from Sutcliffe & Speakman (1), Norit (2) and Chemviron (2), against 3'-FDDU, dimer and anisic acid. A comparison of the ability of each carbon to adsorb 50% of each solute per liter of liquor, revealed that Norit CA1 performs best in removing dimer and anisic acid, while adsorbing the least 3'-FDDU. The carbon powders for testing were each dried at ca. 50° C. in a vacuum oven to constant mass before use.

MOB-3'-FDDU (50.7 g. of 91.7% assay, 0.123 mole) was treated with sodium hydroxide (6.8 g., 0.17 mole) in methanol (357.1 g) for 90 minutes, quenching with water (886 g), and acidifying to pH 1–2 with concentrated hydrochloric acid (20.3 g of 35.4% w/w. 0.19 mole). After filtering the methyl anisic ester with a P40 sinter funnel, the filtrate was washed with toluene (2×170 g), to give 1291.4 g of aqueous methanol solution. 50 g portions of this solution were stirred with xg. of each carbon for 90 minutes, and then filtered through a Whatman microfibre filter. Samples of the filtrate were taken for hplc assay to determine the adsorption isotherms. By calculation the ultimate capacity of each carbon for each solute was derived. The best carbon is that which removes the most dimer and anisic acid and the least 3'-FDDU. A comparison of the carbons tested is shown in the Table below.

| | Carbon (g) per liter for 50% solute removal | | | | |
|---|---|---|---|---|---|
| Solute | DCL226 | CA1 | GB1 | 114A | PWA |
| Dimer | 9.9 | 9.5 | 11.1 | 11.9 | 13.5 |
| Anisic Acid | 7.6 | 8.2 | 5.9 | 3.8 | 6.2 |
| 3'-FDDU | 8.0 | 29.8 | 2.2 | 6.4 | 30.2 |

DCL226: Sutcliffe and Speakman
CA1: Norit
GB1: Norit
114A: Chemviron
PWA: Chemviron These results show that CA1 (Norit) requires the least carbon per liter for the removal of the dimer.

EXAMPLE 4

MOB'-3-FDDU (50.7 g of 91.7% assay–0.123 mole) was treated with sodium hydroxide (6.8 g–0.17 mole) in methanol (357 g) for 90 minutes, quenching with water (886 g) and acidifying to pH=1.2 with concentrated hydrochloric acid (20.3 g of 35.4% w/w–0.19 mole). After filtering the methyl anisic ester with a sinter funnel, the filtrate was washed with toluene (2×170 g) to give 1291.4 g of aqueous methanolic solution with the following assay by HPLC:

3'-FDDU: 2146×10$^{-3}$% (97.9)

Dimer: 27×10$^{-3}$% (1.23)

Anisic acid: 18.5×10$^{-3}$% (0.85)

50 g portions of this liquor were stirred with 0.25 g of CA1 activated carbon (Norit) for 90 minutes, then filtered through a Whatman microfibre filter and the filtrate analysed again by HPLC (assay):

| | % Total | Recovery/Initial |
|---|---|---|
| 3'-FDDU: 1802 × 10$^{-3}$% | 98.6 | 84% |
| Dimer: 17.8 × 10$^{-3}$% | 0.97 | 66% |
| Anisic acid: 7.9 × 10$^{-3}$% | 0.43 | 42% |

EXAMPLE 5

Carbon treatment on crude 3'-FDDU using water solvent

Crude 3'-FDDU (4.74 g at 92%) was charged to a 250 ml round bottom flask and dissolved in 187 g of deionised water to give a 2.5% w/w 3'-FDDU solution. Activated carbon, grade Norit CA1 (2.24 g), was transferred to this and reflux applied for 3 hours followed by hot filtration (80°–90° C.) through a sinter funnel. Analysis (HPLC) before and after carbon treatment are shown in the following Table (assay) with an 83% recovery in 3'-FDDU:

| | 3'-FDDU | Dimer | Anisic Acid |
|---|---|---|---|
| INPUT | 91.8% | 2.01% | — |
| OUTPUT | 96.2% | 0.50% | — |

The hot filtrate was reduced in volume by stripping out 90% by weight of the input water under vacuum at 65°–70° C. A yield of 73% by mass was recovered of pure 3'-FDDU (solid) by cooling-filtration.

I claim:

1. A method of purifying crude 3'-FDDU (2',3'dideoxy-3'-fluorouridine containing anisic acid and a dimer which comprises contacting an aqueous or aqueous methanolic solution of crude 3'-FDDU with adsorbent carbon.

2. A method according to claim 1 wherein the said carbon is an activated carbon.

3. A method according to claim 1 wherein said contact with absorbent carbon is carried out batchwise or in a continuous process using a column of adsorbent.

4. A method according to claim 1 wherein said contact is maintained for 10 min to 15 hours.

5. A method according to claim 4, wherein said contact is maintained for 1 to 4 hours.

6. A method according to claim 1 wherein the amount of carbon used is 0.1 to 5wt % based on the weight of the solution.

7. A method according to claim 1 wherein the contact takes place at a temperature from ambient temperature to 100° C.

8. A process according claim 1 wherein said aqueous or aqueous methanolic solution is washed with toluene prior to contact with the adsorbent carbon.

9. A process according to claim 1 wherein crude 3'-FDDU in solid form has been washed with acetone prior to dissolution in water or aqueous methanol.

10. A composition containing 3'-fluoro-2',3'-dideoxyuridine (3'-FDDU) and less than 1% anisic acid purified by the method of claim 2.

11. A composition containing 3'-fluoro-2',3'-dideoxyuridine (3'-FDDU) and less than 1% anisic acid purified by the method of claim 3.

12. A composition containing 3'-fluoro-2',3'-dideoxyuridine (3'-FDDU) and less than 1% anisic acid purified by the method of claim 4.

13. A composition containing 3'-fluoro-2',3'-dideoxyuridine (3'-FDDU) and less than 1% anisic acid purified by the method of claim 6.

14. A composition containing 3'-fluoro-2',3'-dideoxyuridine (3'-FDDU) and less than 1% anisic acid purified by the method of claim 7.

15. A composition containing 3'-fluoro-2',3'-dideoxyuridine (3'-FDDU) and less than 1% anisic acid purified by the method of claim 8.

16. A composition containing 3'-fluoro-2',3'-dideoxyuridine (3'-FDDU) and less than 1% anisic acid purified by the method of claim 9.

* * * * *

UNITED STATES PATENT AND TRADEMARK OFFICE
CERTIFICATE OF CORRECTION

PATENT NO. : 5,783,688
DATED : July 21, 1998
INVENTOR(S) : Fenner

It is certified that error appears in the above-identified patent and that said Letters Patent is hereby corrected as shown below:

Column 6, line 62, please insert the following claim :

-- 17. A composition containing 3'-fluoro-2'3'-dideoxyuridine (3'-FDDU) and less than 1% anisic acid purified by the method of claim 1.--

Signed and Sealed this

Eleventh Day of May, 1999

Attest:

Q. TODD DICKINSON

Attesting Officer     Acting Commissioner of Patents and Trademarks